United States Patent

Tobiki et al.

[11] 3,951,955
[45] Apr. 20, 1976

[54] PENICILLINS SUBSTITUTED WITH HETEROCYCLIC GROUPS

[75] Inventors: Hisao Tobiki, Toyonaka; Kozo Shimago, Takarazuka; Shigeru Okano, Ibaragi; Toshiaki Komatsu; Toyozo Katsura, both of Takarazuka; Yasushi Taira, Minoo; Yasuko Eda, Toyonaka, all of Japan

[73] Assignee: Sumitomo Chemical Company, Limited, Japan

[22] Filed: July 25, 1974

[21] Appl. No.: 491,693

Related U.S. Application Data

[60] Division of Ser. No. 292,325, Sept. 26, 1972, Pat. No. 3,864,329, which is a continuation-in-part of Ser. No. 213,745, Dec. 29, 1971, abandoned.

[30] Foreign Application Priority Data

Dec. 29, 1970   Japan............................ 45-124374
Dec. 29, 1970   Japan............................ 45-124377

[52] U.S. Cl............................. 260/239.1; 424/271
[51] Int. Cl.².......................................... C07D 499/44
[58] Field of Search.............................. 260/239.1

[56] References Cited
UNITED STATES PATENTS 3,770,722   11/1973   Bright et al. ............... 260/239.1

*Primary Examiner*—Nicholas S. Rizzo
*Attorney, Agent, or Firm*—Stewart and Kolasch, Ltd.

[57] ABSTRACT

A penicillin of the formula:

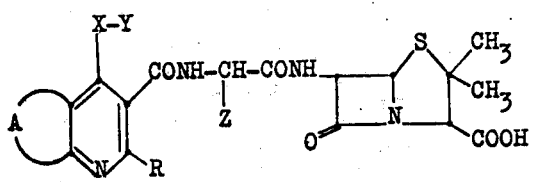

wherein A is a substituted or unsubstituted condensed aromatic carbocyclic or heterocyclic ring, R is hydrogen or lower alkyl, X is oxygen or sulfur, Y is hydrogen, lower alkyl, lower alkanoyl or lower alkoxycarbonyl and Z is phenyl or thienyl which can be produced by reacting 6-aminopenicillanic acid or its ester with a carboxylic acid of the formula:

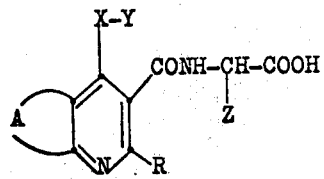

wherein A, R, X, Y and Z are each as defined above or its reactive derivative. The said penicillin and its non-toxic salts have a broad antimicrobial spectrum against various gram-positive and gram-negative bacteria, and they exhibit characteristically a strong antimicrobial activity against *Pseudomonas*.

15 Claims, No Drawings

PENICILLINS SUBSTITUTED WITH HETEROCYCLIC GROUPS

This application is a division of copending application Ser. No. 292,325, filed Sept. 26, 1972 now U.S. Pat. No. 3,864,329 which, in turn, is a continuation-in-part application of Ser. No. 213,745, filed on Dec. 29, 1971, now abandoned.

This invention relates to penicillins and their production. More particularly, it relates to novel derivatives of 6-($\alpha$-aminophenylacetamido)-penicillanic acid and 6-($\alpha$-aminothienylacetamido)-penicillanic acid and their production.

As is well known, 6-($\alpha$-aminophenylacetamido)-penicillanic acid (i.e. ampicillin) inhibits the growth of various gram-positive and gram-negative bacteria but does not exert any appreciable antimicrobial activity against *Pseudomonas*. In Japanese Pat. No. 20986/69, there are described some N-acyl derivatives of said ampicillin as showing a minimal inhibitory concentration of 125 to 250 $\mu$g/ml against *Pseudomonas pyocinea* A or R 59, when determined by the standard test method. The anti-*Pseudomonas* activity of the compounds as described in the working examples is, however, not so high and the antimicrobial activity against other gram-positive and gram-negative bacteria is considerably low. Thus, it may be said that the N-acyl derivatives of ampicillin are less valuable from the practical viewpoint.

As the result of the study seeking novel penicillins which have a broad antimicrobial spectrum and are highly active against gram-positive and gram-negative bacteria including *Pseudomonas*, it has been found that, among various compounds, the penicillins of the following formula characteristically exhibit a noticeable antimicrobial activity against *Pseudomonas:*

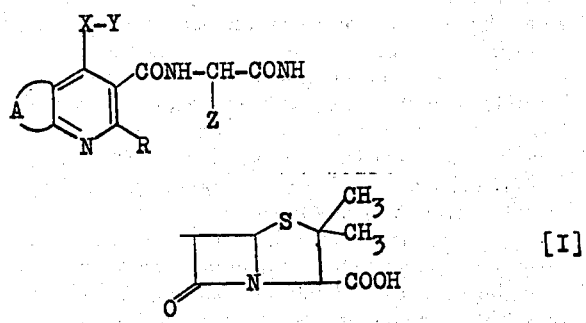

[I]

wherein A is a substituted or unsubstituted condensed aromatic carbocyclic or heterocyclic ring, R is hydrogen or lower alkyl, X is oxygen or sulfur, Y is hydrogen, lower alkyl, lower alkanoyl or lower alkoxycarbonyl and Z is phenyl or thienyl. They exhibit also a high antimicrobial activity against other gram-positive and gram-negative bacteria. This invention is based on the above finding.

Accordingly, it is a basic object of the present invention to provide the penicillins [I] and their non-toxic salts. Another object of this invention is to provide a process for preparing the penicillins [I] and their non-toxic salts. A further object of the invention is to provide the antimicrobial agents useful for controlling various gram-positive and gram-negative bacteria including *Pseudomonas*. These and other objects of the invention will be apparent to those skilled in the art from the foregoing and subsequent descriptions.

In the above formula [I], the condensed aromatic carbocyclic and heterocyclic ring represented by the symbol A may be benzene, naphthalene or a six-membered heteroaromatic ring containing nitrogen as the hetero atom, etc. Examples of the substituent which may be present on such ring are lower alkyl (e.g. methyl, ethyl, propyl, isopropyl, butyl), lower alkoxy (e.g. methoxy, ethoxy, propoxy, buthoxy), lower alkoxycarbonyl (e.g. methoxycarbonyl, ethoxycarbonyl, propoxycarbonyl), hydroxyl, halogen (e.g. chlorine, bromine, iodine, fluorine), halo(lower)alkyl (e.g. chloromethyl, trifluoromethyl), nitro, lower alkylsulfonyl (e.g. methylsulfonyl), mercapto, lower alkylthio (e.g. methylthio, ethylthio, propylthio), lower alkylenedioxy (e.g. methylenedioxy, ethylenedioxy), lower alkylene (e.g. trimethylene, tetramethylene), amino, lower alkylamino (e.g. methylamino, ethylamino, propylamino), di(lower)alkylamino (e.g. dimethylamino, diethylamino, methylethylamino), etc. When the substituent is amino or lower alkylamino, it may be present in any protected form conventionally employed in peptide synthesis, e.g. bearing a protecting group (e.g. acetyl, carbobenzoxy, trichloroethoxycarbonyl, o-nitrophenylsulfenyl) or taking a protected structure (e.g. enamine). The number of the substituent is usually from 1 to 3, if present.

The term "lower" is intended to mean the group having up to 8 carbon atoms throughout the specification. Particularly preferred are those having 1 to 4 carbon atoms for the alkyl moiety and the alkylene moiety.

The non-toxic salts of the penicillins [I] are, for instance, the alkali metal salts (e.g. sodium, potassium salts), the alkaline earth metal salts (e.g. calcium, barium, magnesium salts), the substituted and unsubstituted ammonium salts, the arginine salt, etc. All these are conventional salts in the related art field.

According to the present invention, the penicillin [I] can be produced by reacting 6-aminopenicillanic acid or its ester with a carboxylic acid of the formula:

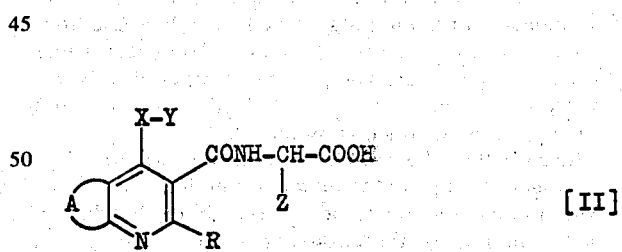

[II]

wherein A, R, X, Y and Z are each as defined above or its reactive derivative.

One of the starting materials is 6-aminopenicillanic acid or its ester. The ester is required to recover carboxyl by hydrogenation, hydrolysis or any other appropriate chemical treatment after accomplishment of the amidation, and specific examples thereof include the trialkylsilyl ester, trichloroethyl ester, lower alkanoyloxymethyl ester, phenacyl ester, etc. All these esters are conventional in the related art field.

The other starting material is the carboxylic acid [II] or its reactive derivative. Examples of the reactive derivative of the carboxylic acid [II] are the acid halide, acid azide, acid anhydride, mixed acid anhydride, active ester (e.g. p-nitrophenyl ester, N-hydroxysuccinimide ester), active thioester, active thioacid anhydride, active amide (e.g. imidazole amide, triazole amide), etc.

The carboxylic acid [II] or its ester may be produced, for instance, by reacting an amino acid of the formula:

[III]

wherein Z is as defined above or its ester with a carboxylic acid of the formula:

[IV]

wherein A, R, X and Y are each as defined above or its reactive derivative in an appropriate solvent (e.g. methanol, ethanol, dichloromethane, chloroform, dioxane, acetone, dimethylformamide) in the presence of a basic substance (e.g. pyridine, trimethylamine) at a temperature from about −50° to 80°C, if necessary, followed by hydrolysis.

The reaction between 6-aminopenicillanic acid or its ester and the carboxylic acid [II] or its reactive derivative is usually effected in an inert solvent such as a polar solvent (e.g. dichloromethane, chloroform, acetone, tetrahydrofuran, dioxane, acetonitrile, dimethylformamide) or a non-polar solvent (e.g. benzene, toluene), or their mixtures. The inert solvent may sometimes include water. The reaction temperature is normally from about −50° to 80°C, and the execution under cooling with ice is preferred.

In case that the carboxylic acid [II] wherein Y is hydrogen is subjected to amidation in the reacted form with an alkanoyl halide or alkoxycarbonyl halide, one molar amount of the carboxylic acid is first reacted with at least two molar amounts of the acylating agent in the presence of at least two molar amounts of a basic substance and then the resulting product is reacted with 6-aminopenicillanic acid or its ester to give the penicillin [I] wherein Y is lower alkanoyl or lower alkoxycarbonyl. Hydrolysis of the latter with an organic or inorganic basic substance, particularly with an aqueous solution of alkali metal carbonate (e.g. sodium carbonate, potassium carbonate), affords the corresponding penicillin [I] wherein Y is hydrogen.

The penicillin [I] can be also produced by reacting 6-(α-amino-substituted-acetamido)-penicillanic acid of the formula:

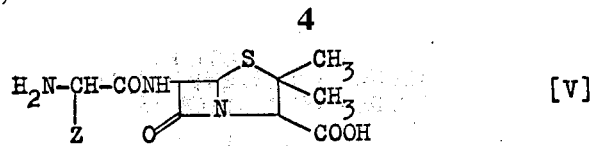

[V]

wherein Z is as defined above or its ester with the carboxylic acid [IV] or its reactive derivative.

One of the starting materials is 6-(α-amino-substituted-acetamido)-penicillanic acid [V] or its ester. Thee ester is required to recover carboxyl by hydrogenation, hydrolysis or any other appropriate chemical treatment after accomplishment of the amidation, and specific examples thereof include the trialkylsilyl ester, trichloroethyl ester, lower alkanoyloxymethyl ester, phenacyl ester, etc. All these esters are conventional in the related art field.

The other starting material is the carboxylic acid [IV] or its reactive derivative. Examples of the reactive derivative of the carboxylic acid [IV] are the acid halide, acid azide, acid anhydride, mixed acid anhydride, active ester (e.g. p-nitrophenyl ester, N-hydroxysuccinimide ester), active thioester, active thioacid anhydride, active amide (e.g. imidazole amide, triazole amide), etc.

The reaction between the 6-(α-amino-substituted-acetamido)-penicillanic acid [V] or its ester and the carboxylic acid [IV] or its reactive derivative is usually effected in an inert solvent as mentioned above. The reaction temperature is ordinarily from about −50° to 80°C, and the performance under cooling with ice is favorable.

In case that the carboxylic acid [IV] wherein Y is hydrogen is subjected to amidation in the reacted form with an alkanoyl halide or alkoxycarbonyl halide, one molar amount of the carboxylic acid is first reacted with at least two molar amounts of the acylating agent in the presence of at least two molar amounts of a basic substance and then the resulting product is reacted with the 6-(α-amino-substituted-acetamido)-penicillanic acid [V] or its ester to give the penicillin [I] wherein Y is lower alkanoyl or lower alkoxycarbonyl. Hydrolysis of the latter with an organic or inorganic basic substance, particularly with an aqueous solution of alkali metal carbonate (e.g. sodium carbonate, potassium carbonate), affords the corresponding penicillin [I] wherein Y is hydrogen.

In case that the carboxylic acid [IV] wherein Y is hydrogen is subjected to amidation in the reacted form with phosgene, thionyl chloride, phosphorus trichloride or the like, one molar amount of the carboxylic acid is first reacted with one molar amount of the reagent in the presence of at least two molar amounts of a basic substance and then the resulting product is reacted with the 6-(α-amino-substituted-acetamido)-penicillanic acid [V] or its ester to give the penicillin [I] wherein Y is hydrogen.

Further, the penicillin [I] wherein the ring A is substituted with amino or lower alkylamino can be produced from the corresponding compound bearing a group convertible to amino or lower alkylamino on the ring A. Examples of the group convertible to amino or lower amino are nitro, protected amino, protected lower alkylamino, etc. The protecting group in case of protected amino and protected lower alkylamino may be those as are conventionally employed in peptide synthesis. When the substituent is nitro, it can be converted into amino by a per se conventional hydrogenation procedure in the presence or absence of any appropriate catalyst. When the substituent is protected amino or protected lower alkylamino, there is usually employed hydrogenation or hydrolysis. In any case, the adoption of a mild reaction condition is necessary for avoiding the opening of the β-lactam ring in the penicillin nucleus.

The thus produced penicillin [I] may be converted into any non-toxic salt by a per se conventional procedure.

As stated above, the penicillins [I] and their non-toxic salts according to this invention are useful as antimicrobial agents against various gram-positive and gram-negative bacteria including Pseudomonas and may be used in the same manner as applied to conventional antimicrobial agents such as ampicillin.

Practical and presently preferred embodiments of the present invention are illustratively shown in the following Examples.

EXAMPLE 1

Preparation of
D-(−)-α-(4-ethoxycarbonyloxyquinoline-3-carbonamido)-benzylpenicillin:

1. D-(−)-α-(4-Hydroxyquinoline-3-carbonamido)-phenylacetic acid.

Dichloromethane (50 ml) is added to 4-hydroxyquinoline-3-carboxylic acid (2.5 g), and 29.6 % phosgene-dichloromethane (4.4 g) is added thereto under cooling. After the dropwise addition of triethylamine (2.7 g) at −20° to −25°C, D-(−)-α-phenylglycine ethyl ester hydrochloride (2.86 g) and triethylamine (1.4 g) are added to the resulting mixture. Stirring is continued at −15° to −20°C for 1 hour. The reaction mixture is washed with water, a solution of sodium hydroxide (1 g) in water (20 ml) is added thereto and stirring is effected at 40°C for 1 hour. The water layer is adjusted to pH 1 with hydrochloric acid to precipitate crude crystals. Recrystallization of the crude crystals from dioxane affords D-(−)-α-(4-hydroxyquinoline-3-carbonamido)-phenylacetic acid (1.1 g). M.P. 195°C.

2. D-(−)-α-(4-Ethoxycarbonyloxyquinoline-3-carbonamido)-benzylpenicillin:

The phenylacetic acid (1 g) as obtained in (1) is admixed with triethylamine (0.63 g) and dichloromethane (30 ml), and ethyl chlorocarbonate (0.70 g) is added thereto at −10°C. Stirring is continued at the same temperature as above for 30 minutes. 6-Aminopenicillanic acid triethylamine salt (0.985 g) is added to the resulting mixture at −10°C, and stirring is continued at the same temperature as above for 3 hours. A dilute aqueous solution of sodium carbonate is added to the reaction mixture, and the water layer is separated and adjusted to pH 2.0 with 1 N hydrochloric acid. The resulting solution is extracted three times with ethyl acetate (50 ml), and the extract is washed with water, dried over anhydrous magnesium sulfate and concentrated at 25°C under reduced pressure. The residue is crystallized from ether to give D-(−)-α-(4-ethoxycarbonyloxyquinoline-3-carbonamido)-benzylpenicillin (1.3 g). M.P. 156.5° to 158.5°C (decomp.).

EXAMPLE 2

Preparation of
D-(−)-α-(4-ethoxycarbonyloxyquinoline-3-carbonamido)-benzylpenicillin:

To a mixture of 4-hydroxyquinoline-3-carboxylic acid (1.88 g), dioxane (50 ml), acetone (10 ml) and triethylamine (2.02 g), there is dropwise added ethyl chlorocarbonate (2.16 g) while cooling. After stirring for 30 minutes, D-(−)-α-aminobenzylpenicillin triethylamine salt (4.50 g) is added to the resulting mixture, and stirring is further continued for 1 hour. Then, a dilute aqueous solution of sodium hydrogen carbonate is added to the reaction mixture, and the resultant mixture is shaken with ethyl acetate. The water layer is separated and acidified to pH 2 with dilute hydrochloric acid. The precipitate is extracted with ethyl acetate. The extract is washed with water, dried over anhydrous magnesium sulfate and concentrated at 25°C. The separated crystals are washed with ether and dried on phosphorus pentoxide to give D-(−)-α-(4-ethoxycarbonyloxyquinoline-3-carbonamido)-benzylpenicillin (4.70 g). Purity (determined by iodometry), 88.5 %.

EXAMPLE 3

Preparation of
D-(−)-α-(4-hydroxyquinoline-3-carbonamido)-benzylpenicillin:

D-(−)-α-(4-ethoxycarbonyloxyquinoline-3-carbonamido)-benzylpenicillin (1.18 g) is dissolved in an aqueous solution of sodium carbonate while cooling, and the resulting solution is stirred for 1 hour. After acidifying to pH 2 with dilute hydrochloric acid, the precipitate is extracted with ethyl acetate, and the extract is washed with water, dried over anhydrous magnesium sulfate and concentrated at 25°C. The separated crystals are washed with ether and dried over phosphorus pentoxide to give D-(−)-α-(4-hydroxyquinoline-3-carbonamido)-benzylpenicillin (0.95 g). Purity (determined by iodometry), 90.3 %.

EXAMPLE 4

Preparation of
D-(−)-α-(7-methyl-4-hydroxy-1,8-naphthyridine-3-carbonamido)-benzylpenicillin potassium salt:

To D-(−)-α-(7-methyl-4-hydroxy-1,8-naphthyridine-3-carbonamido)-phenylacetic acid (M.P. 275°C (decomp.)) (2 g) prepared from 7-methyl-4-hydroxy-1,8-naphthyridine-3-carboxylic acid (M.P. 288°C (decomp.)) in the same procedure as in Example 1 (1), dichloromethane (50 ml) and triethylamine (1.2 g) are added, and ethyl chlorocarbonate (1.35 g) is dropwise added thereto at 0° to 5°C. After stirring for 30 minutes, 6-aminopenicillanic acid triethylamine salt (1.9 g) is added to the resulting mixture, and stirring is further continued at the same temperature as above for 3 hours. The reaction mixture is shaken with a dilute aqueous solution of sodium carbonate. The aqueous layer is separated, adjusted to pH 2 with hydrochloric acid while cooling and extracted with ethyl acetate. The extract is washed with water and dried over anhydrous magnesium sulfate. Then, a 50 % n-butanol solution of potassium 2-ethylhexanoate is added thereto. The separated crystals are collected by filtration and washed with ether to give D-(−)-α-(7-methyl-4-hydroxy-1,8-naphthyridine-3-carbonamido)-benzylpenicillin potassium salt (2 g). M.P. 222° to 224°C (decomp.). Purity (determined by iodometry), 85 %.

EXAMPLE 5

Preparation of D-(−)-α-(7-methyl-4-ethoxycarbonyloxy-1,8-naphthyridine-3-carbonamido)-benzylpenicillin:

To a mixture of 4-hydroxy-7-methyl-1,8-naphthyridine-3-carboxylic acid (0.41 g), dioxane (45 ml), acetone (10 ml) and triethylamine (0.41 g), ethyl chloroformate (0.44 g) is dropwise added while cooling. After stirring for 30 minutes, D-(−)-α-aminobenzylpenicillin triethylamine salt (0.90 g) is added thereto, and the resultant mixture is stirred further for 1 hour. The reaction mixture is admixed with a dilute aqueous solution of sodium hydrogen carbonate and shaken with ethyl acetate. The water layer is adjusted to pH 2 with dilute hydrochloric acid, and the precipitate is extracted with ethyl acetate. The extract is washed with water, dried over anhydrous magnesium sulfate and concentrated at 25°C. The separated crystals are washed with ether and dried over phosphorus pentoxide to give D-(−)-α-(7-methyl-4-ethoxycarbonyloxy-1,8-naphthyridine-3-carbonamido)-benzylpenicillin (0.85 g).

EXAMPLE 6

Preparation of D-(−)-α-(4-pivaloyloxyquinoline-3-carbonamido)-benzylpenicillin:

To a mixture of D-(−)-α-(4-hydroxyquinoline-3-carbonamido)-phenylacetic acid (M.P. 195°C) (1 g), dichloromethane (30 ml) and triethylamine (0.63 g), pivaloyl chloride (0.85 g) is dropwise added at 0° to 5°C. After stirring for 20 minutes, 6-aminopenicillanic acid triethylamine salt (1 g) is added thereto, and the resultant mixture is stirred at the same temperature as above for 5 hours. The reaction mixture is extracted with ethyl acetate. The extract is washed with dilute hydrochloric acid and water, dried over anhydrous magnesium sulfate and concentrated under reduced pressure. The obtained crystals (1.05 g) of D-(−)-α-(4-pivaloyloxyquinoline-3-carbonamido)-benzylpenicillin are purified by dissolving into a small amount of ethyl acetate and adding ether thereto so as to precipitate crystals. Purity (determined by iodometry), 89.5 %.

EXAMPLE 7

Preparation of D-(−)-α-(2-methyl-6,7-methylenedioxy-4-hydroxyquinoline-3-carbonamido)-benzylpenicillin potassium salt:

(1) D-(−)-α-(2-Methyl-6,7-methylenedioxy-4-hydroxyquinoline-3-carbonamido)-phenylacetic acid.

To a mixture of 2-methyl-6,7-methylenedioxy-4-hydroxyquinoline-3-carboxylic acid (M.P. 340°C (decomp.)) (2 g), dichloromethane (60 ml) and triethylamine (1.65 g), ethyl chlorocarbonate (1.8 g) is dropwise added thereto at −10°C. After 30 minutes, D-(−)-α-phenylglycine ethyl ester hydrochloride (1.7 g) and triethylamine (0.85 g) are added thereto at the same temperature as above, and stirring is effected for 4 hours. The reaction mixture is treated as in Example 1 (1) to give D-(−)-α-(2-methyl-6,7-methylenedioxy-4-hydroxyquinoline-3-carbonamido)-phenylacetic acid (1.5 g) as crystals. M.P. 250°C (decomp.).

(2) D-(−)-α-(2-Methyl-6,7-methylenedioxy-4-hydroxyquinoline-3-carbonamido)-benzylpenicillin potassium salt.

To a mixture of D-(−)-α-(2-methyl-6,7-methylenedioxy-4-hydroxyquinoline-3-carbonamido)-phenylacetic acid (1 g), dichloromethane (30 ml) and triethylamine (0.53 g), pivaloyl chloride (0.72 g) is added thereto at 0° to 3°C. After stirring for 20 minutes, 6-aminopenicillanic acid triethylamine salt (0.8 g) is added, and the resulting mixture is stirring at 0° to 5°C for 5 hours. The reaction mixture is treated as in Example 4 to give D-(−)-(2-methyl-6,7-methylenedioxy-4-hydroxyquinoline-3-carbonamido)-benzylpenicillin potassium salt (1.2 g) as crystals. Purity (determined by iodometry), 82 %. Water content, 6.7 %.

EXAMPLES 8 to 60

In the same procedure as above, there are produced the following penicillins [I]:

| Example No. | Chemical structure | Purity (determined by iodometry) |
|---|---|---|
| 8 | 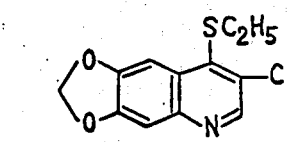 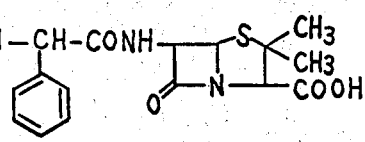 | 89.5 % |
| 9 | 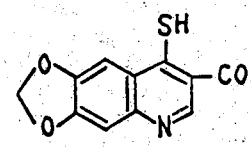 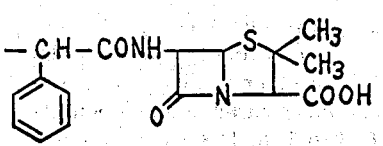 | 78.6 % |

-continued
| Example No. | Chemical structure | Purity (determined by iodometry) |
|---|---|---|
| 10 | 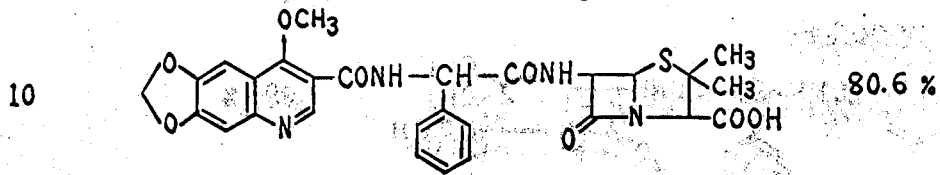 | 80.6 % |
| 11 | 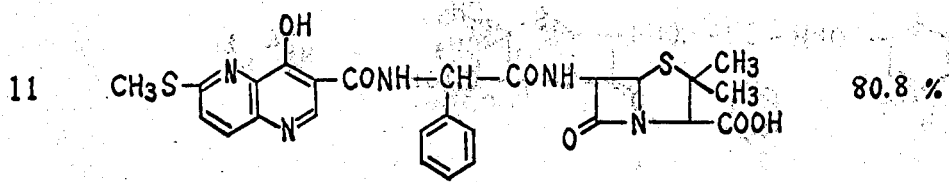 | 80.8 % |
| 12 | 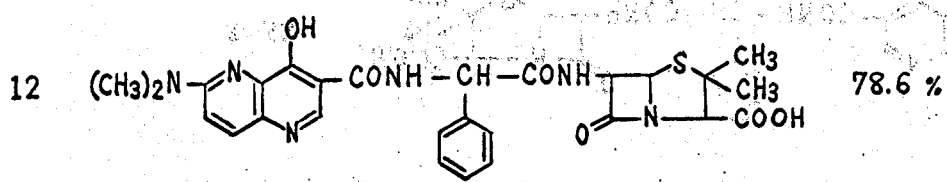 | 78.6 % |
| 13 | 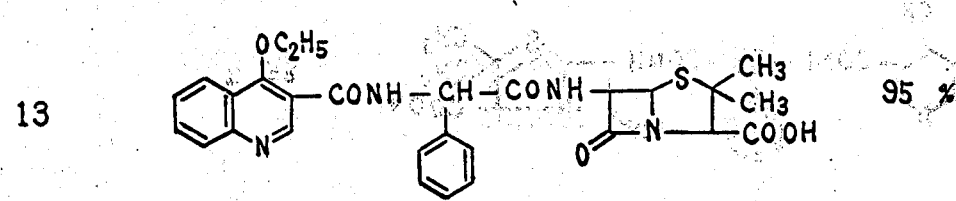 | 95 % |
| 14 | 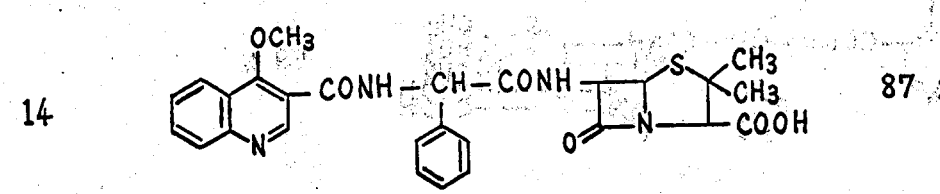 | 87 % |
| 15 | 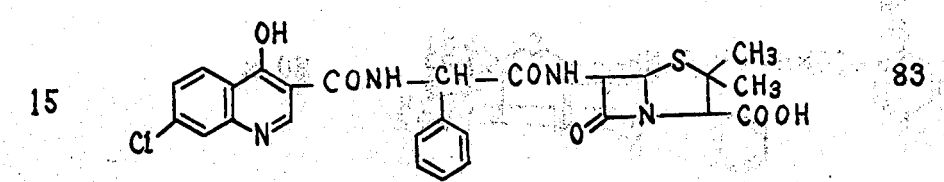 | 83 % |
| 16 | 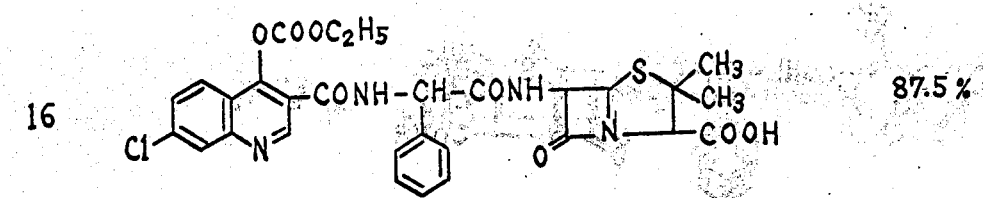 | 87.5 % |

-continued

| Example No. | Chemical structure | Purity (determined by iodometry) |
|---|---|---|
| 17 | 7-CH$_3$O, 4-OCOOC$_2$H$_5$ quinoline-3-CONH-CH(C$_6$H$_5$)-CONH-penicillanic acid | 89 % |
| 18 | 7-CH$_3$O, 4-OH quinoline-3-CONH-CH(C$_6$H$_5$)-CONH-penicillanic acid | 84 % |
| 19 | 6-CH$_3$O, 4-OH quinoline-3-CONH-CH(C$_6$H$_5$)-CONH-penicillanic acid | 85 % |
| 20 | 7-F$_3$C, 4-OH quinoline-3-CONH-CH(C$_6$H$_5$)-CONH-penicillanic acid | 86 % |
| 21 | 7-O$_2$N, 4-OH quinoline-3-CONH-CH(C$_6$H$_5$)-CONH-penicillanic acid | 79 % |
| 22 | 7-CH$_3$SO$_2$, 4-OH quinoline-3-CONH-CH(C$_6$H$_5$)-CONH-penicillanic acid | 80 % |
| 23 | 6-CH$_3$CONH, 4-OH quinoline-3-CONH-CH(C$_6$H$_5$)-CONH-penicillanic acid | 87 % |

-continued
| Example No. | Chemical structure | Purity (determined by iodometry) |
|---|---|---|
| 24 | 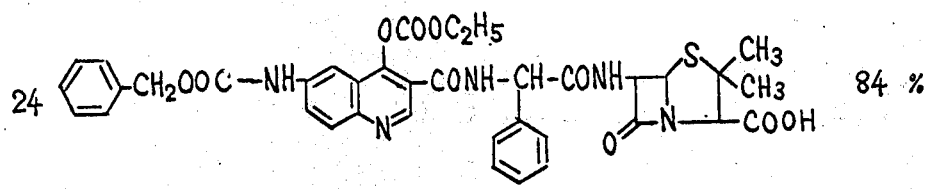 | 84 % |
| 25 | 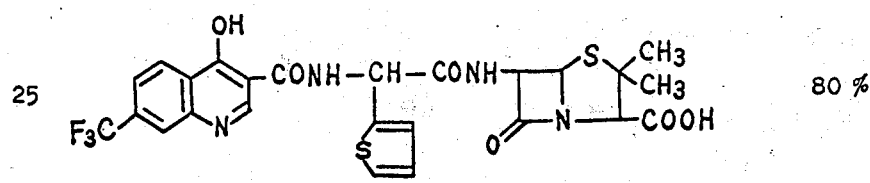 | 80 % |
| 26 | 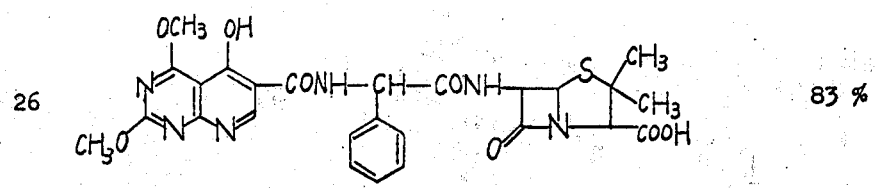 | 83 % |
| 27 | 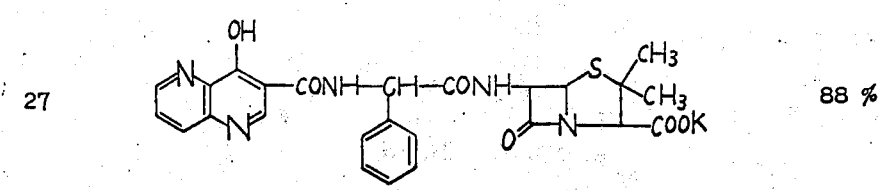 | 88 % |
| 28 | 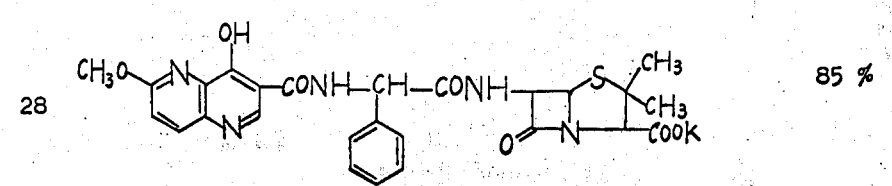 | 85 % |
| 29 | 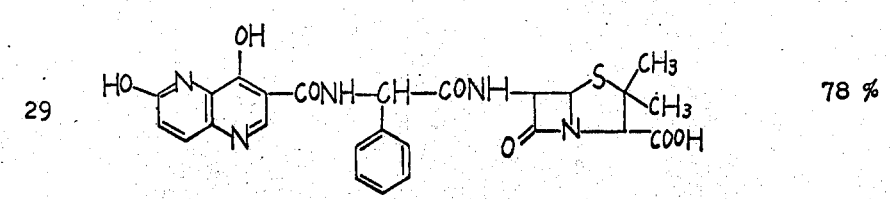 | 78 % |
| 30 | 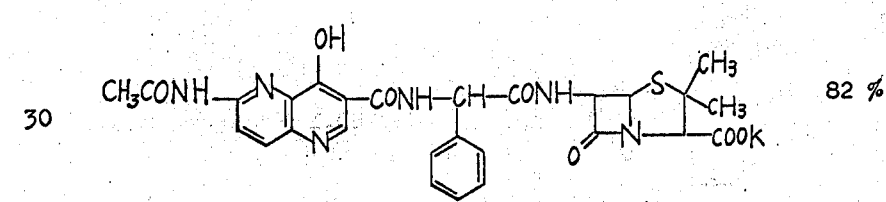 | 82 % |

| Example No. | Chemical structure | Purity (determined by iodometry) |
|---|---|---|
| 31 | 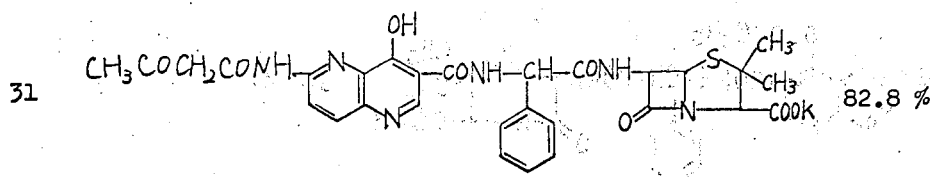 | 82.8 % |
| 32 | 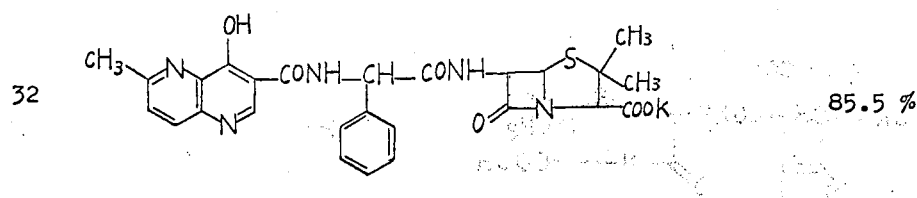 | 85.5 % |
| 33 | 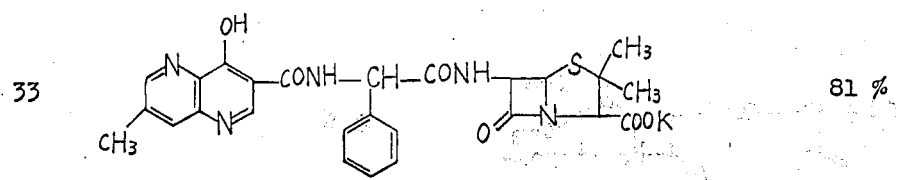 | 81 % |
| 34 | 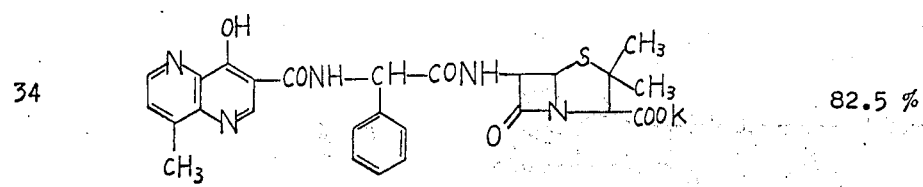 | 82.5 % |
| 35 | 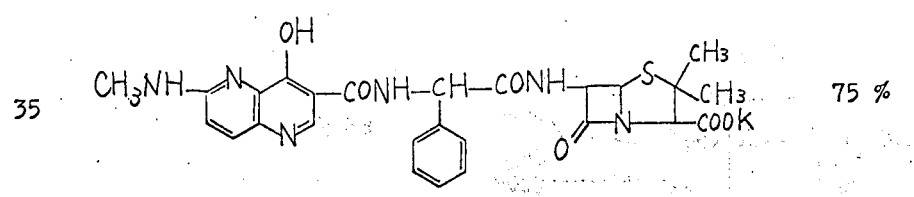 | 75 % |
| 36 | 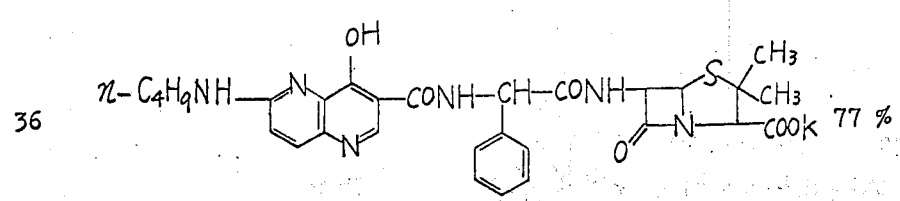 | 77 % |
| 37 | 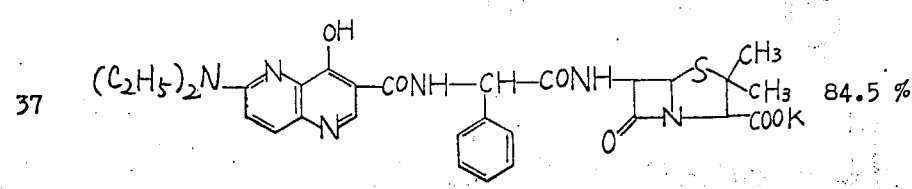 | 84.5 % |
| 38 | 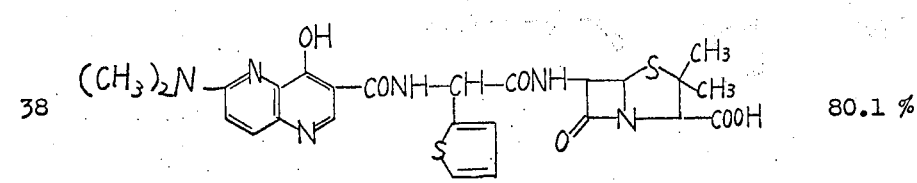 | 80.1 % |

-continued
| Example No. | Chemical structure | Purity (determined by iodometry) |
|---|---|---|
| 39 | 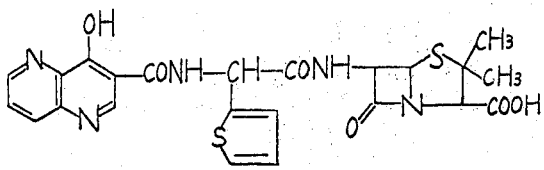 | 87.3 % |
| 40 | 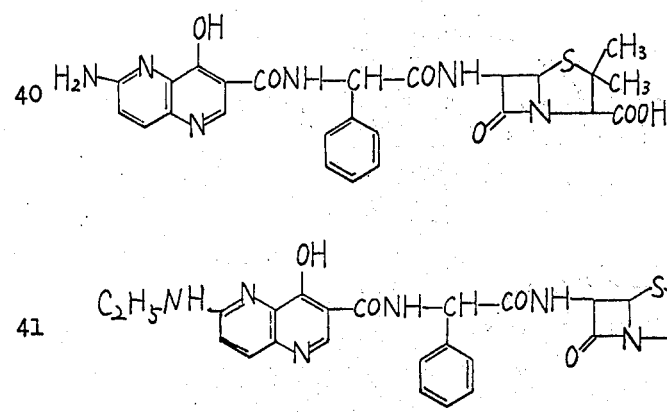 | 75.4 % |
| 41 | 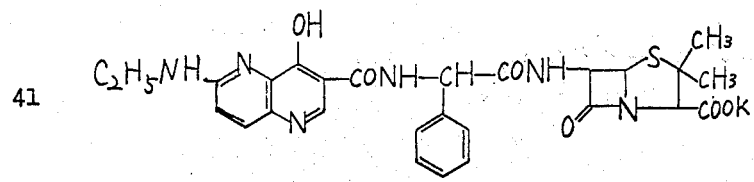 | 72 % |
| 42 | 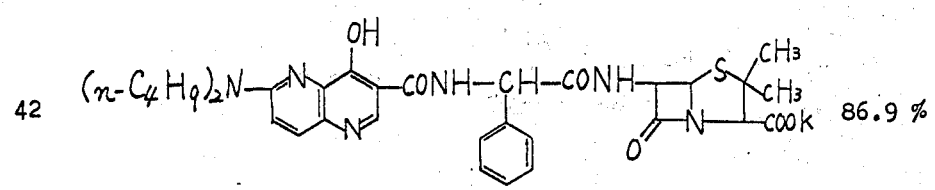 | 86.9 % |
| 43 | 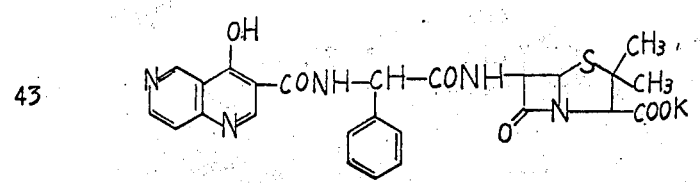 | 84 % |
| 44 | 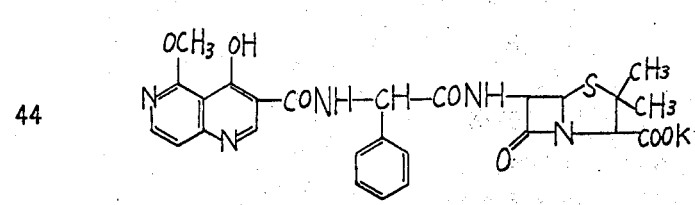 | 88 % |
| 45 | 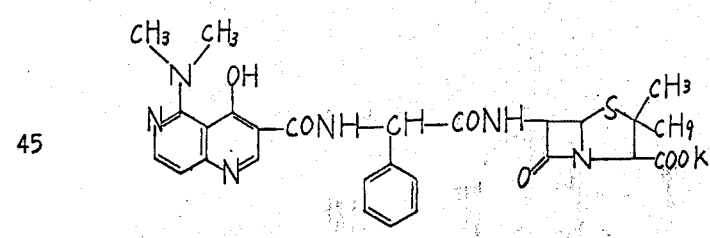 | 89.1 % |
| 46 | 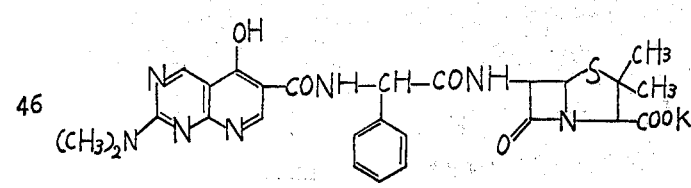 | 79.5 % |

-continued
| Example No. | Chemical structure | Purity (determined by iodometry) |
|---|---|---|
| 47 | 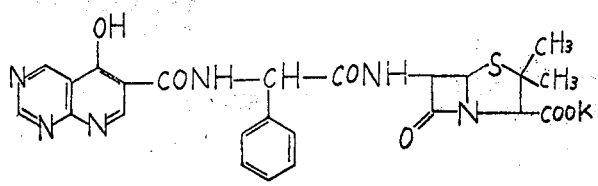 | 84.1 % |
| 48 | 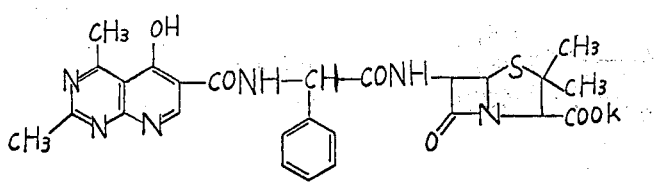 | 89.1 % |
| 49 | 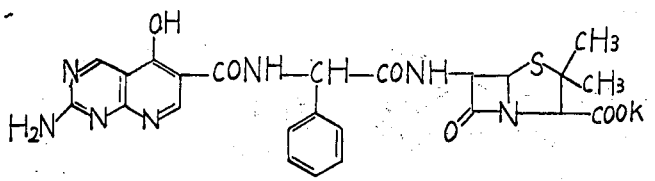 | 78 % |
| 50 | 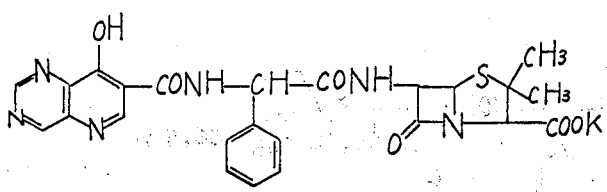 | 87.3 % |
| 51 | 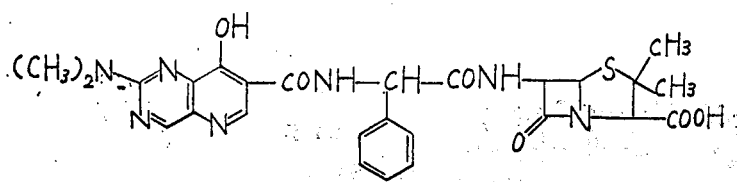 | 89.7 % |
| 52 | 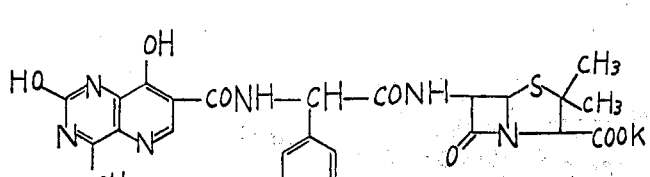 | 75.9 % |
| 53 | 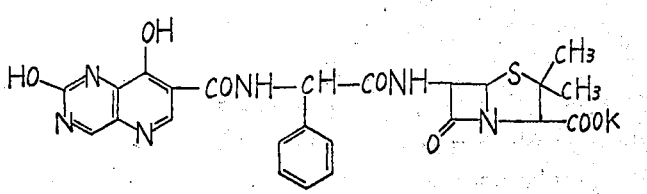 | 84 % |
| 54 | 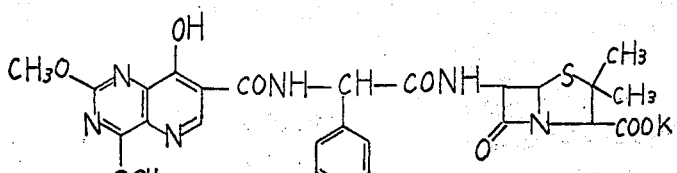 | 82.8 % |

| Example No. | Chemical structure | Purity (determined by iodometry) |
|---|---|---|
| 55 | 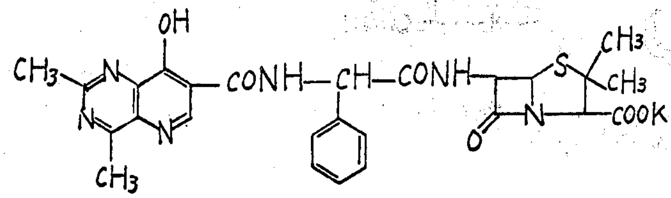 | 87.4 % |
| 56 | 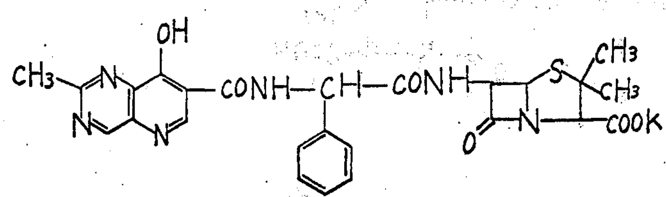 | 88 % |
| 57 | 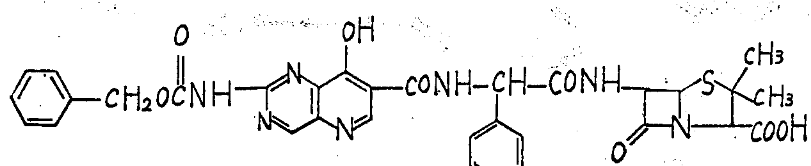 | 80.2 % |
| 58 | 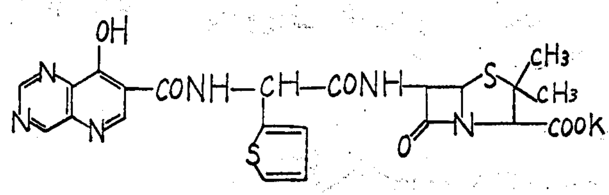 | 87.1 % |
| 59 | 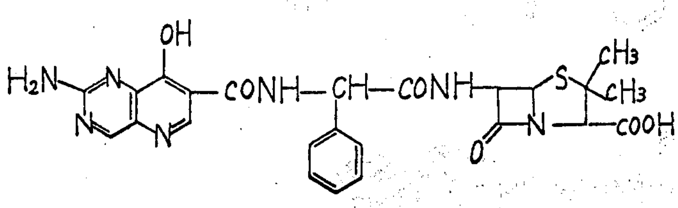 | 78 % |
| 60 | 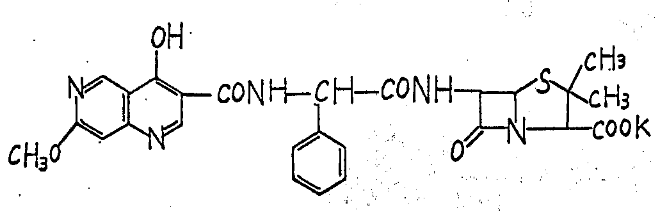 | 84.3 % |
When the penicillins in Examples 21 and 24 are catalytically reduced, the following products are respectively obtained:
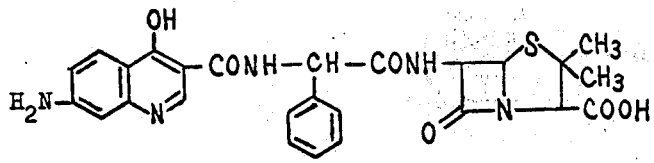

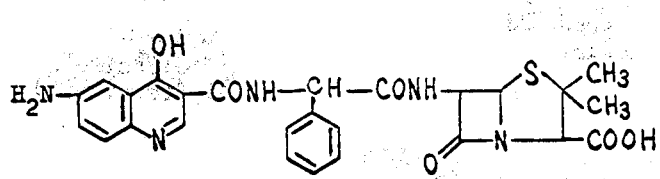
In the substantially same manner as above, there are also produced the following penicillins [I]:
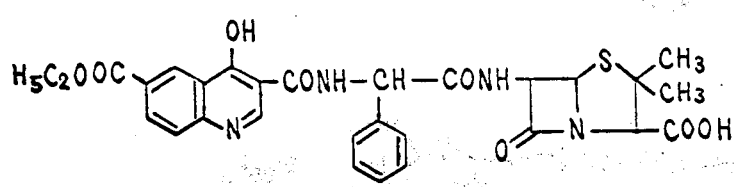
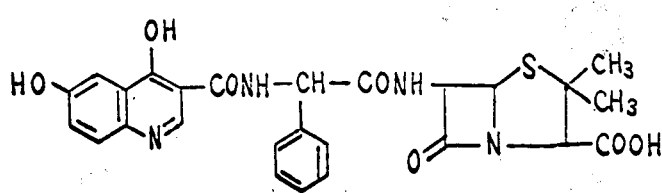
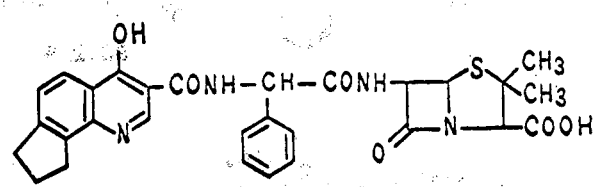
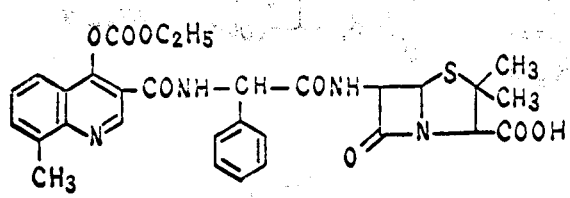
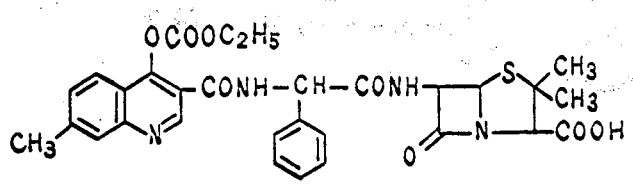
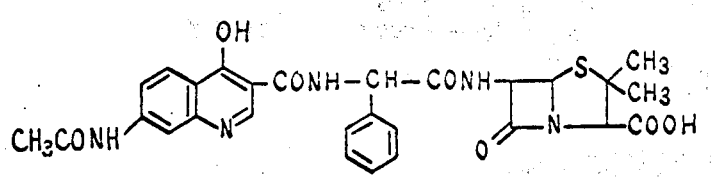
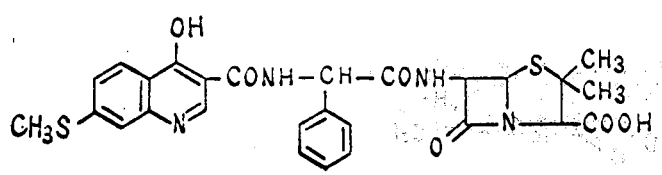

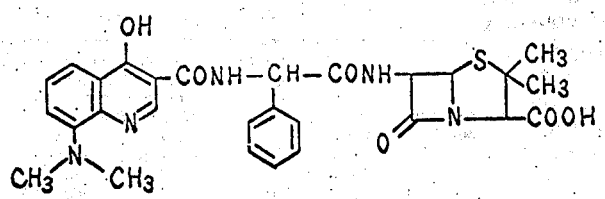
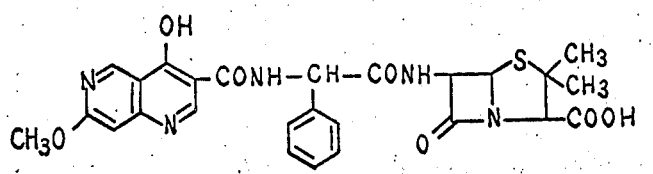
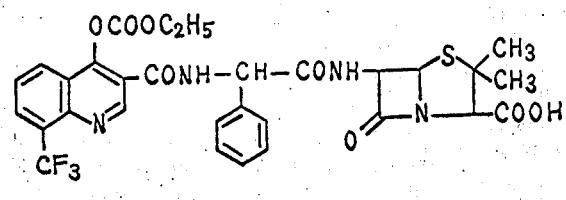
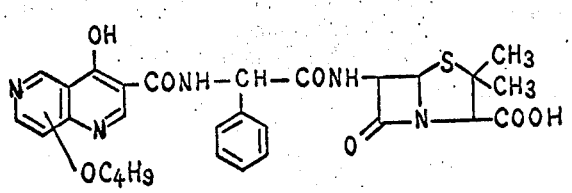
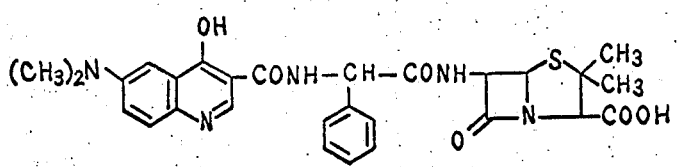
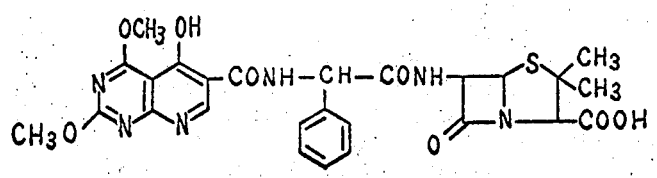
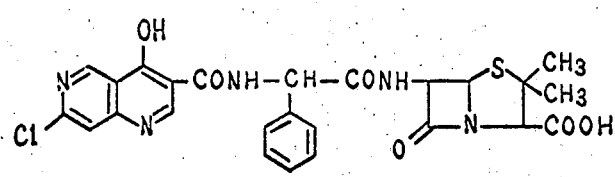
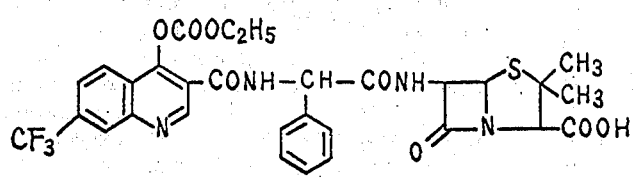

The production of the penicillins [I] can be confirmed by elementary analysis, purity analysis (by iodometry), infrared absorption spectrum and so on. Particularly effective is NMR analysis. Thus, the proton signals (Ha, Hb) in the two amide bonds as seen in the following structure for the penicillins [I] characteristically shift depending on the kind of the substituent Y:

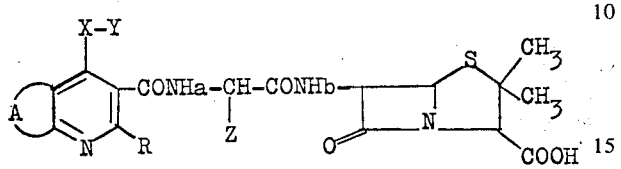

When measured in hexadeuterodimethylsulfoxide using an instrument "Varian T-60", both the Ha and Hb in case of Y being alkyl shift to 540–570 Hz. In case of Y being alkanoyl or alkoxycarbonyl, Ha and Hb shift respectively to 630–640 Hz and 540–570 Hz. In case of Y being hydrogen, Ha and Hb shift respectively to 650–680 Hz and 540–570 Hz.

When determined according to the agar dilution method, the penicillins [I] afford the minimal inhibitory concentrations as shown in the following Table 1:

Table 1:

| Example No. | Minimal Inhibitory Concentrations of Penicillins [I] against Pathogenic Microorganisms (in vitro) MIC (µg/ml) | | | | |
|---|---|---|---|---|---|
| | Staphylococcus aureus 209P | Escherichia coli NIHJ | Proteus miravilis 2425 | Klebsiella pneumoniae 602 | Pseudomonas aeruginosa 104 |
| 1 | 0.2 | 6.25 | 1.56 | — | 3.13 |
| 3 | 0.2 | 6.25 | 3.13 | 1.56 | 6.25 |
| 4 | 0.78 | 12.5 | 6.25 | — | 6.25 |
| 5 | 0.78 | 12.5 | 6.25 | — | 12.5 |
| 6 | 0.1 | 6.25 | 1.56 | — | 3.13 |
| 7 | 0.2 | 12.5 | 6.25 | — | 12.5 |
| 8 | 0.2 | 12.5 | 12.5 | — | 25 |
| 9 | 0.2 | 6.25 | 3.13 | — | 3.13 |
| 10 | 0.2 | 12.5 | 25 | — | 25 |
| 11 | 0.1 | 6.25 | 3.13 | — | 3.13 |
| 12 | 0.1 | 6.25 | 3.13 | — | 3.13 |
| 13 | 0.2 | 12.5 | 25 | — | 50 |
| 14 | 0.2 | 25 | 12.5 | 25 | 12.5 |
| 15 | 0.2 | 3.13 | 1.56 | 0.39 | 3.13 |
| 16 | 0.2 | 6.25 | 3.13 | 0.39 | 3.13 |
| 17 | 0.2 | 3.13 | 1.56 | 0.39 | 3.13 |
| 18 | 0.39 | 6.25 | 1.56 | 0.78 | 6.25 |
| 19 | 0.39 | 6.25 | 1.56 | 0.78 | 6.25 |
| 20 | 0.39 | 12.5 | 3.13 | 0.39 | 6.25 |
| 21 | 0.39 | 12.5 | 6.25 | 0.78 | 12.5 |
| 22 | 0.39 | 12.5 | 3.13 | 0.39 | 6.25 |
| 23 | 0.78 | 12.5 | 3.13 | 3.13 | 12.5 |
| 24 | 0.39 | 12.5 | 12.5 | 1.56 | 12.5 |
| 25 | 0.39 | 12.5 | 3.16 | — | 6.25 |
| 26 | 0.78 | 3.13 | 3.13 | 3.13 | 3.13 |
| 27 | 0.78 | 1.56 | 3.13 | 6.25 | 3.13 |
| 28 | 0.78 | 1.56 | 1.56 | 3.13 | 3.13 |
| 29 | 1.56 | 1.56 | 3.13 | 3.13 | 3.13 |
| 30 | 0.78 | 3.13 | 6.25 | 3.13 | 6.25 |
| 31 | 0.78 | 3.13 | 6.25 | 6.25 | 6.25 |
| 32 | 0.78 | 1.56 | 1.56 | 3.13 | 3.13 |
| 33 | 1.56 | 3.13 | 3.13 | 3.13 | 6.25 |
| 34 | 1.56 | 3.13 | 3.13 | 6.25 | 3.13 |
| 35 | 0.78 | 1.56 | 6.25 | 3.13 | 3.13 |
| 36 | 1.56 | 1.56 | 3.13 | 3.13 | 3.13 |
| 37 | 0.78 | 0.78 | 1.56 | 0.78 | 3.13 |
| 38 | 0.78 | 1.56 | 1.56 | 1.56 | 6.25 |
| 39 | 0.78 | 1.56 | 3.13 | 3.13 | 6.25 |
| 40 | 0.78 | 1.56 | 1.56 | 1.56 | 3.13 |
| 41 | 0.78 | 3.13 | 6.25 | 6.25 | 6.25 |
| 42 | 1.56 | 3.13 | 3.13 | 3.13 | 3.13 |
| 43 | 0.78 | 12.5 | 12.5 | 6.25 | 6.25 |
| 44 | 0.78 | 12.5 | 6.25 | 12.5 | 12.5 |
| 45 | 0.78 | 6.25 | 6.25 | 3.13 | 12.5 |
| 46 | 1.56 | 3.13 | 3.13 | 1.56 | 3.13 |
| 47 | 0.78 | 3.13 | 6.25 | 3.13 | 3.13 |
| 48 | 0.78 | 12.5 | 6.25 | 3.13 | 12.5 |
| 49 | 0.78 | 6.25 | 6.25 | 6.25 | 12.5 |
| 50 | 0.78 | 1.56 | 1.56 | 0.78 | 3.13 |
| 51 | 0.78 | 0.78 | 1.56 | 0.78 | 3.13 |
| 52 | 1.56 | 3.13 | 3.13 | 3.13 | 6.25 |
| 53 | 1.56 | 3.13 | 6.25 | 6.25 | 6.25 |
| 54 | 1.56 | 6.25 | 3.13 | 3.13 | 6.25 |
| 55 | 0.78 | 3.13 | 3.13 | 1.56 | 3.13 |
| 56 | 0.78 | 3.13 | 6.25 | 3.13 | 3.13 |
| 57 | 1.56 | 6.25 | 3.13 | 3.13 | 6.25 |
| 58 | 0.78 | 1.56 | 3.13 | 1.56 | 3.13 |
| 59 | 0.78 | 3.13 | 3.13 | 1.56 | 3.13 |
| 60 | 1.56 | 6.25 | 3.13 | 3.13 | 12.5 |
| Ampicillin | 0.2 | 6.25 | 3.13 | 50 | >200 |

From the above results, it may be noted that the penicillins [I] are of nearly equal level to ampicillin in the antimicrobial activity against various microorganisms and characteristically much stronger than the latter in the antimicrobial activity against Pseudomonas

What is claimed is:

1. A penicillin of the formula:

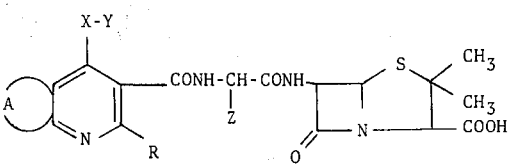

wherein A is an unsubstituted benzene or pyrimidine ring or a benzene or pyrimidine ring substituted with one or more members selected from the group consisting of lower alkyl, lower alkoxy, lower alkoxycarbonyl, hydroxyl, halogen, halo(lower)alkyl, nitro, lower alkylsulfonyl, lower alkylthio, lower alkylenedioxy, lower alkylene, amino, lower alkylamino, di(lower)alkylamino, acetamido, benzyloxycarbonylamino, trichloroethoxycarbonylamino and o-nitrophenylsulfenylamino, R is hydrogen or lower alkyl, X is oxygen or sulfur, Y is hydrogen, lower alkyl, lower alkanoyl or lower alkoxycarbonyl and Z is phenyl or thienyl, and non-toxic pharmaceutically acceptable salts thereof.

2. A penicillin of the formula:

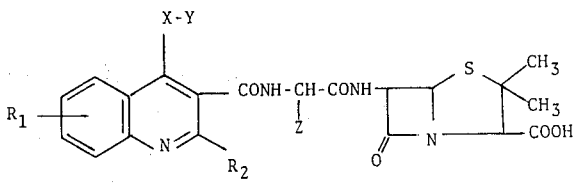

wherein $R_1$ is hydrogen, lower alkyl, lower alkoxy, hydroxyl, halo(lower)alkyl, halogen, nitro, amino, acetamido, benzyloxycarbonylamino, di(lower)alkylamino, lower alkylthio, lower alkylsulfonyl, lower alkoxycarbonyl, lower alkylenedioxy or lower alkylene, $R_2$ is hydrogen or lower alkyl, X is oxygen or sulfur, Y is hydrogen, lower alkoxycarbonyl or lower alkanoyl and Z is phenyl or thienyl, and non-toxic pharmaceutically acceptable salts thereof.

3. A penicillin of the formula:

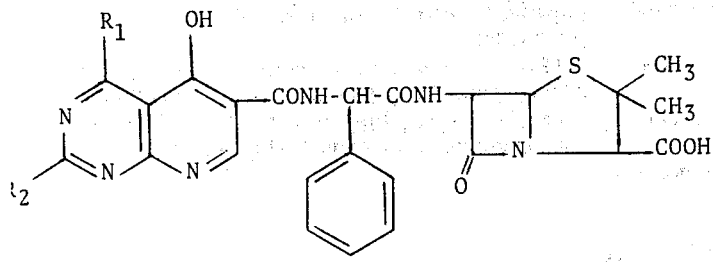

wherein $R_1$ and $R_2$ are each hydrogen, lower alkyl, lower alkoxy, amino or di(lower)alkylamino, and non-toxic pharmaceutically acceptable salts thereof.

4. A penicillin of the formula:

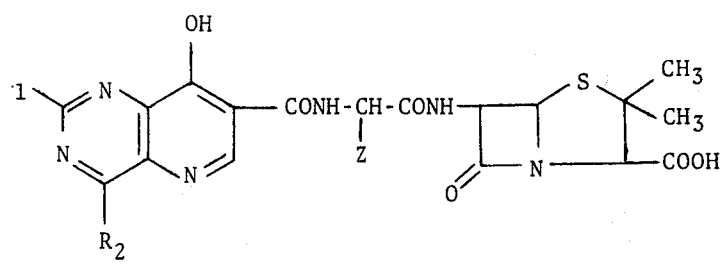

wherein $R_1$ and $R_2$ are each hydrogen, lower alkyl, lower alkoxy, hydroxyl, amino or benzyloxycarbonylamino and Z is phenyl or thienyl, and non-toxic pharmaceutically acceptable salts thereof.

5. A penicillin of the formula:

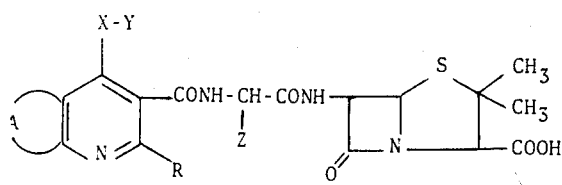

wherein A is an unsubstituted benzene or pyrimidine ring or a benzene or pyrimidine ring substituted with one or more members selected from the group consisting of lower alkyl, lower alkoxy, hydroxyl, halo(lower)alkyl, halogen, nitro, amino, acetamido, benzyloxycarbonylamino, di(lower)alkylamino, lower alkylthio, lower alkylsulfonyl, lower alkoxycarbonyl, lower alkylenedioxy or lower alkylene, R is hydrogen or lower alkyl, X is oxygen or sulfur, and Z is phenyl or thienyl, and non-toxic pharmaceutically acceptable salts thereof.

6. A penicillin of the formula:

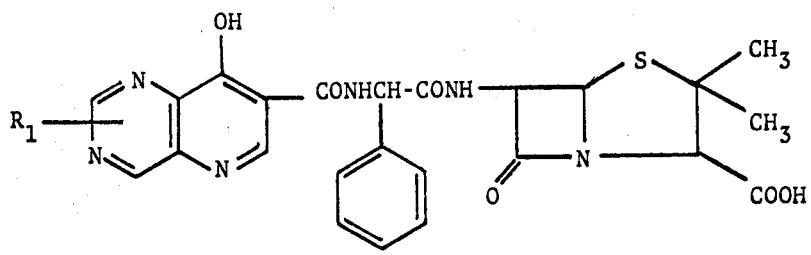

wherein $R_1$ is hydrogen, lower alkyl, lower alkoxy, lower alkylthio, amino, lower alkylamino, di(lower)alkylamino or acetyl-, carbobenzoxy-, trichloroethoxycarbonyl- or o-nitrophenylsulfenylamino.

7. A penicillin of the formula:

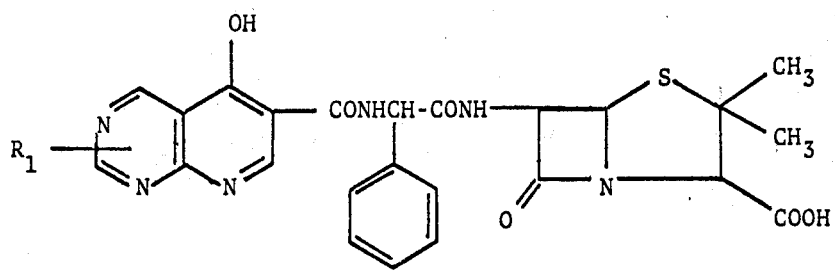

wherein $R_1$ is hydrogen, lower alkyl, lower alkoxy, lower alkylthio, amino, lower alkylamino, di(lower)alkylamino or acetyl-, carbobenzoxy-, trichloroethoxycarbonyl- or o-nitrophenylsulfenylamino.

8. D-(−)-α-(4-Ethoxycarbonyloxyquinoline-3-carbonamido)-benzylpenicillin.

9. D-(−)-α-(4-Hydroxyquinoline-3-carbonamido)-benzylpenicillin.

10. D-(−)-α-(7-Chloro-4-hydroxyquinoline-3-carbonamido)-benzylpenicillin.

11. D-(−)-α-(5-Hydroxypyrido[2,3-d]pyrimidine-6-carbonamido)-benzylpenicillin.

12. D-(−)-α-(8-Hydroxypyrido[3,2-d]pyrimidine-7-carbonamido)-benzylpenicillin.

13. D-(−)-α-(2-Dimethylamino-8-hydroxypyrido[3,2-d]-pyrimidine-7-carbonamido)-benzylpenicillin.

14. D-(−)-α-(2-Methyl-8-hydroxypyrido[3,2-d]pyrimidine-3-carbonamido)-benzylpenicillin.

15. D-(−)-α-(4-Hydroxypyrido[3,2-d]pyrimidine-3-carbonamido)-2-thienylmethylpenicillin.

* * * * *